United States Patent [19]

Russo

[11] 4,182,347
[45] Jan. 8, 1980

[54] AIR INHALATION FLOW RATE MEASURING DEVICE

[76] Inventor: Ronald D. Russo, 111 S. Barranca St., Apt. 327, West Covina, Calif. 91791

[21] Appl. No.: 881,396

[22] Filed: Feb. 27, 1978

[51] Int. Cl.² .............................................. A61B 5/08
[52] U.S. Cl. ...................................... 128/725; 272/99
[58] Field of Search ............... 128/185, 201, 716, 725; 272/99 R; 73/194 M, 207, 209

[56] References Cited
U.S. PATENT DOCUMENTS

| 2,099,842 | 11/1937 | Connell | 73/209 X |
| 2,827,008 | 3/1958 | Hodge | 73/207 X |
| 3,416,371 | 12/1968 | Locke | 73/209 |
| 4,060,074 | 11/1977 | Russo | 128/2.08 |

Primary Examiner—Henry J. Recla
Attorney, Agent, or Firm—Bruce & McCoy

[57] ABSTRACT

An air inhalation flow rate measuring device for exercising the respiratory musculature and increasing the lung capacity of the user, including an air flow column having a plurality of column segments with individual air flow indicators residing in each segment which move to indicate air intake flow rates when a user inhales air through the device.

13 Claims, 7 Drawing Figures

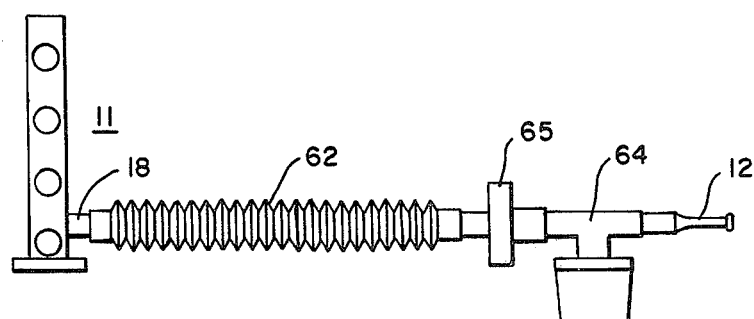
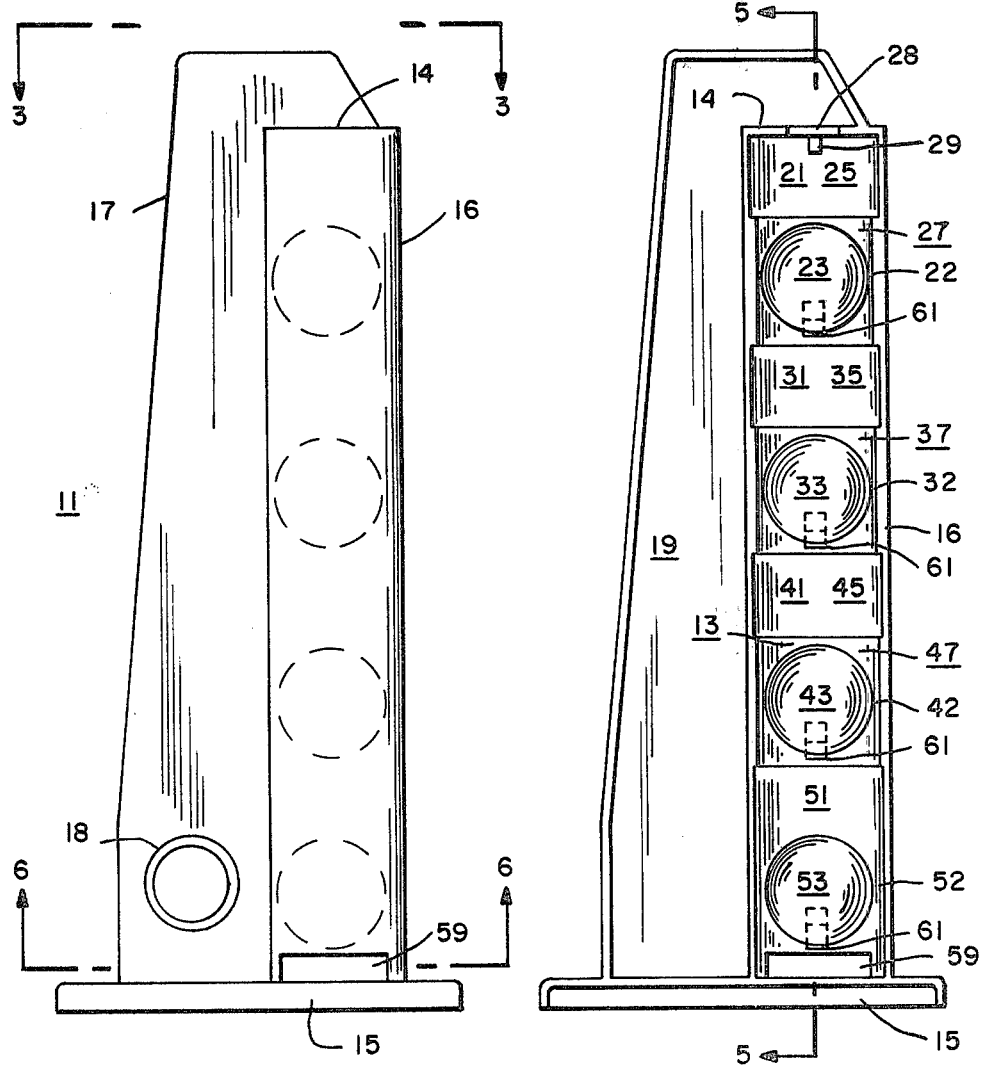

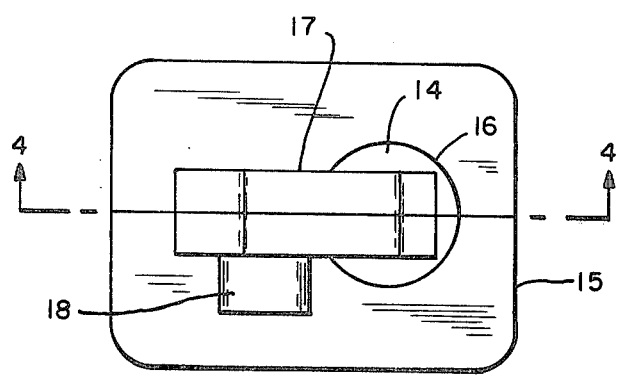
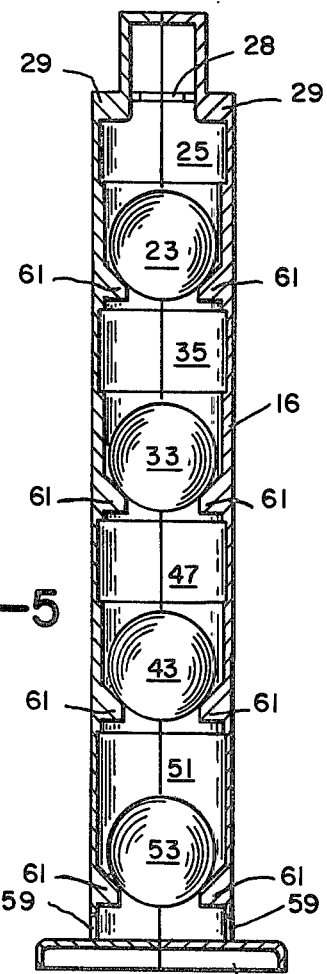
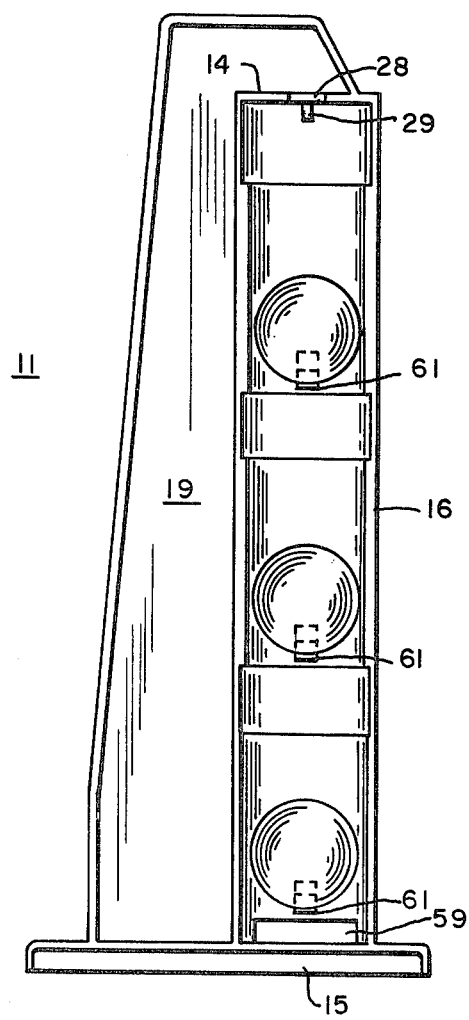
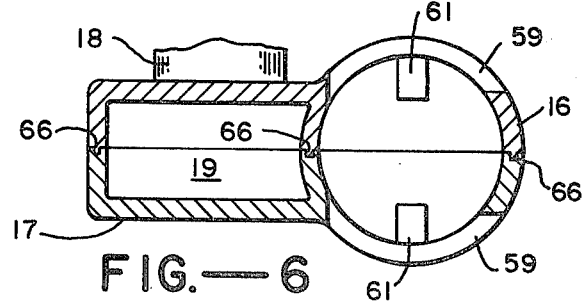
FIG.—3
FIG.—5
FIG.—7
FIG.—6

AIR INHALATION FLOW RATE MEASURING DEVICE

CROSS REFERENCES TO RELATED APPLICATIONS

Applications related to the instant application are a continuation-in-part application to the U.S. Pat. No. 4,060,074, issued Nov. 29, 1977 to the assignee of the present inventor and an application filed concurrently herewith.

BACKGROUND OF THE INVENTION

1. Field of the Invention

The present invention relates to air flow indicators and more particularly to a device for measuring human breath inhalation flow rates. The present invention also relates to inhalation devices which provide an incentive to improve lung capacity and to exercise respiratory musculature. Particularly with patients experiencing post surgical pain, and inactive, obese, and geriatric patients, it is sometimes necessary to utilize a program of breathing exercise to maintain or increase the patient's lung capacity. Due to patient medication or lethargy, it has been found that an exerciser with incentive capabilities produces the best results. One type of incentive device is an air flow rate indicator which shows the patient he is performing his exercises correctly.

2. Description of the Prior Art

The prior art U.S. Pat. No. 4,060,074 depicts an incentive breathing device wherein several vertical air flow columns stand proximate each other. Each air flow column has an air intake orifice that opens directly to the atmosphere, a uniform cross-sectional area throughout its length, an air flow rate indicator located therein, and an air outlet that opens to an air duct which is in pneumatic communication with each of the other columns and with an air inhalation means. The user inhales through the air inhalation means and thereby withdraws air from all of the columns simultaneously. As inhaled air flows through all columns at an increasing rate, an air flow rate indicator rises to the top of a column at a precalibrated air inhalation rate to indicate the air flow rate that is being achieved. The indicator, upon rising to the top of the chamber, seals the air outlet for that chamber. As the flow rate of inhaled air continues to increase, indicators in the remaining columns will then sequentially rise to the tops of their columns and each column will be sealed except the last.

The air flow rate indicators are typcially lightweight spheres of slightly smaller outer diameter than the inner diameter of the column within which they reside. The gap between the sphere and the column wall is the parameter which is varied to calibrate the device, and a column for measuring high flow rates would have a larger gap, than a column for measuring low flow rates. It is the flow rate of air which is drawn through the column that causes the flow indicator to rise in the moving air to the top of the column and seal the air outlet at the top of the column.

Several problems have been found with this prior art device which the present invention overcomes. The problems exist because the top common air duct services all columns, each of which has an air intake orifice. Upon initial use, this construction results in the total air flow being shared through all columns, and it thus requires a substantial total air flow rate before the air flow rate in a single column is sufficient to lift a first sphere. Experience has shown that a minimum gap of approximately 40 thousandths of an inch (0.1 centimeters) is required to insure that a sphere will not become hung up in its column. This minimum gap is described in the preferred embodiment of the prior art, and its use results in a minimum air flow rate for the prior art of approximately 600 cubic centimeters per second. As the gap cannot be decreased, it is therefore the case that the prior art is unable to measure air flow rates that are below approximately 600 cubic centimeters per second. The prior art has attempted to circumvent this low air flow rate design limitation by making provision for the tilting of the device from its normal vertical orientation; however this solution is obviously less satisfactory than the new configuration of the present invention.

Significantly, low air flow rates of 150–500 cubic centimeters per second have been found to be the most beneficial to seriously afflicted users as they result in a laminar type of air flow to the user's lungs, and it is believed that laminar air flow causes better air exchange in the lungs. Thus, the prior art device is not configured to measure the type of air flow required by those who are most seriously in need of an incentive inhalation device, and a tilting of the device from its normal vertical orientation must be accomplished to attempt such a measurement.

The above-mentioned problems are overcome by the present invention. Low flow rates are easily obtainable through the utilization of the single air flow column. There is but a single air intake orifice, and thus all of the inhaled air must pass through each calibrated segment of the air flow column. There is no inhaled air that bypasses the low rate air flow indicator to undermine its accuracy, and a large range of air flow rates is easily obtained by the stacking of several differently calibrated air flow column segments to comprise the single air flow column. The ability to provide low flow rates for the user results in the user being able to obtain the laminar flow characteristics that have been found to be most desirable.

Further advantages of the present invention will become apparent when the preferred embodiment of the present invention is considered in conjunction with the accompanying drawings.

SUMMARY OF THE INVENTION

The present invention is an improved air inhalation flow rate measuring device which provides an incentive for post surgical, inactive, obese, and geriatric type patients to exercise their respiratory muscles and increase their lung capacity. It is designed to encourage deep, slow, prolonged inspiration which promotes maximum alveolar inflation to increase lung capacity and to help prevent atelactesis. It measures a wide range of inhalation rates to benefit the widest range of potential users and provide the most benefits to a single user.

In brief, the present invention includes a structure which has a vertical air flow column which is comprised of a series of column segments each of which has uniform cross-sectional dimensions along a portion of its length, but each of which is formed with a different uniform cross-sectional dimension from the others. The structure also includes an air inhalation means that is in pneumatic communication with the air column such that a user inhaling through the inhalation means will draw air up through the column. The device includes a plurality of air flotation elements, each of which is movably disposed within a different column segment, and each of which may be separately raised within its column segment, and each of which may be raised by a different air inhalation flow rate through the column.

OBJECTS OF THE INVENTION

It is therefore an important object of the present invention to provide a respiratory exercising device which has sensitivity at low inhalation rates but yet may accurately measure a wide range of inhalation rates.

It is another object of the present invention to provide a device which has a simple readout of inhalation air flow rates.

It is a further object of the present invention to provide a device which has little restriction to the air flow and permits a more efficient and repetitive operation by the user.

It is yet another object of the present invention to provide a device which is easy to use by patients and which provides incentives for respiratory exercise.

It is yet a further object of the present invention to provide a device which may be inexpensively manufactured and which has features adaptable to several desirable accessory items.

It is still another object of the present invention to provide a device which permits a full free uninterrupted flow of air during breathing exercise, and which suspends a plurality of measuring elements in a free float state to provide a visual gauge of achievement as an incentive to the user.

Other objects and advantages of the invention will become apparent when it is considered in conjunction with the accompanying drawings.

BRIEF DESCRIPTION OF THE DRAWINGS

FIG. 1 is an end view of the improved air inhalation flow rate measuring device of the present invention shown connected to a length of flexible hollow tubing, dual valve, nebulizer, and mouthpiece;

FIG. 2 is a front elevation of the present invention;

FIG. 3 is a top plan view of the present invention taken along lines 3—3 of FIG. 2;

FIG. 4 is a front elevational view of one-half of the present invention taken along lines 4—4 of FIG. 3 which is a natural separation line of the injection molded portions of the preferred embodiment;

FIG. 5 is a cross-sectional view of the present invention taken along the lines 5—5 of FIG. 4;

FIG. 6 is a cross-sectional view of the present invention taken along lines 6—6 of FIG. 2; and FIG. 7 is a cross-sectional view of an alternative embodiment of the present invention taken along the same vertical axis as FIG. 4.

DESCRIPTION OF THE PREFERRED EMBODIMENT

The improved air inhalation flow rate measuring device 11 includes a single vertical air flow column 13 having a top 14, sidewall 16, and a bottom formed by attachment to the base 15, with attached air passage walls 17 which define air inhalation passage 19 that leads from the air outlet 28 to the mouthpiece connection orifice 18.

In the preferred embodiment, the air passage walls 17 are integrally attached to the column 13 and a substantial portion of the air inhalation passage 19 is upright and parallel to it. A top portion of the air inhalation passage laps over and completely encloses the air outlet 28 of the column. The mouthpiece connection orifice 18 allows air to be withdrawn from the column through the air inhalation passage and may include a tubular projection to facilitate the attachment of an air withdrawal means thereto. It is recognized that tubing or the like could be used to permit inhalation through the column 13, so long as the air outlet 28 were enclosed by the tubing. However, the configuration of the air inhalation passage described in the preferred embodiment of the invention has been found to result in a more stable structure since the mouthpiece connection orifice 18 is located near the base of the air inhalation passage. A user pulling on the tubing is more likely to drag the device across its supporting surface than to topple it over, as might occur if the tubing were attached to the top of the column.

Air withdrawal means 62 are attached to the mouthpiece connection orifice 18 to withdraw air from the air inhalation passage. In the preferred embodiment, the air withdrawal means 62 includes flexible, hollow tubing which is attached at one end to the mouthpiece connection orifice 18 and which has a mouthpiece 12 attached to the other end. This flexible, hollow tubing, which may be standard polyethylene or EVA tubing, enables one to use the device at some distance from the upright structure.

The device of this invention may be adaptable to the needs of individual users by the attachment of several accessories. A medicinal dispensing device or nebulizer 64 can be connected to the pneumatic system between the mouthpiece connection orifice and the mouthpiece attached to the tubing. A dual valve 65 may also be connected to the pneumatic system between the mouthpiece connection orifice and the mouthpiece attached to the tubing. By the addition of these accessories, a physician may prescribe a particular medication which is placed in a nebulizer that is attached to the pneumatic system. A dual valve attached to the tubing makes it possible for a user to inhale air through the system with the mouthpiece in place, and then, without removing the mouthpiece from the user's mouth, the user can exhale and the dual valve will shunt the exhaled air into the atmosphere rather than back into the inhalation device. This configuration of accessories would be particularly helpful to a bedridden or weak user.

In the preferred embodiment, the air inhalation passage further comprises air filtering means (not shown) to prevent extraneous matter from being inhaled through the device into the lungs of the user. The air filtering means most preferably is an injection-molded air flow screen which is disposed in the air inhalation passage and covers the mouthpiece connection orifice.

The air flow column 13 includes a plurality of air column segments of which four are shown in the preferred embodiment 21, 31, 41, 51. Each column segment has an air flotation element 23, 33, 43, 53, residing therein and contains wall projections 61 which serve to provide both a lower rest position for the air flotation element in a particular column segment and an upper stop to prevent an air flotation element residing in a lower column segment from rising into a higher column segment. The top-most column segment is provided with a wall projection 29 proximate the air outlet 28, which acts to prevent the top-most air flotation element 23 from sealing the air outlet 28. The bottom most column segment 51 is provided with an air intake orifice 59 located below the rest position of the air flotation element residing therein and connecting the column with the outside atmosphere. In the preferred embodiment, each column segment except the lowest is further divided into an upper free flow section 25, 35, 45 and a lower calibrated uniform portion 27, 37, 47. The cross-sectional area of the free flow section is formed to be larger than its associated lower calibrated uniform portion. The preferred embodiment is formed with a progressive sequence of flow rates, whereby the top most column segment 21 is calibrated to have the lowest air flow rate, and successively lower column segments are each calibrated to have increasingly higher flow rates, with the bottom-most column segment calibrated to have the highest flow rate. However, it is recognized that other sequences could easily be employed.

In operation, the user inhales through a mouthpiece 12 which is attached to the mouthpiece connection orifice 18. Due to the configuration of the system, as air is withdrawn by the user from the mouthpiece 12, new air enters the device through the air intake orifice 59 to replace that which is withdrawn. This replacement air is drawn upwards successively through each column segment, 51, 41, 31, 21, then through the air outlet 28, through the air inhalation passage 19, through the mouthpiece connection orifice 18 and into the mouthpiece 12. The air, as it is drawn upwards through each column segment, must pass successively through the gaps 52, 42, 32, 22, that are formed between the air flotation element and the column segment wall at the lower calibrated uniform portion of the respective column segment. Each gap represents the differential between the cross-sectional dimension of the lower uniform portion and the cross-sectional dimension of the air flotation element residing therein. By means of varying the size of each gap, the lower calibrated uniform portion of each column segment is calibrated such that at a preselected air flow rate the lifting force on the air flotation element, created by the air flowing past it, will cause it to rise within the column segment. The air flotation element will continue to rise within its column segment, provided the user maintains the calibrated air flow rate, until the air flotation element has entered the free flow section of the column segment. The gap between the air flotation element and the column segment wall increases when the air flotation element is located in the free flow section because the cross-sectional dimension of the free flow segment is larger than that of its associated lower calibrated uniform portion. Where the user maintains the calibrated air flow rate, the force on the air flotation element will thus be sufficient to cause it to rise in the lower calibrated uniform portion until it enters the free flow section, whereupon it will cease to rise and commence to float in the moving air stream within the free flow section of the column segment. The air flotation element will not re-enter the lower calibrated uniform portion so long as the user maintains the calibrated air flow rate.

During a typical inhalation effort the air flow rate starts at zero, increases to a maximum and then decreases to zero. As the air inhalation rate increases the top most air flotation element 23 is the first to rise into its free flow section 25, where it remains suspended during the increasing inhalation effort. Upon reaching the precalibrated air flow rate of the second column segment 31, air flotation element 33 will rise into its free flotation section 35, where it remains suspended during the increasing inhalation effort. Upon reaching the precalibrated air flow rates of the remaining column segments in decending order, each air flow element therein will sequentially rise into its free flotation section. The air flotation elements remain suspended in their free flow sections so long as the air flow rate is greater than their respective precalibrated rates. As the air flow rate decreases the air flotation elements each return to their rest positions in their respective lower calibrated uniform portions when the air flow rate is below the precalibrated rate for that column segment. The floating air flotation elements thus indicate to the user the air inhalation rate that is being achieved, and the availability of a plurality of air flotation elements provides the visual cue that acts as an incentive to exercise the respiratory musculature and increase the lung capacity.

In the preferred embodiment, air flow column 13 is formed in a cylindrical shape having a circular cross section. The air flotation elements are formed as identical lightweight spheres, preferably formed of a blow molded polyethylene with a one inch (2.54 centimeters) outer diameter. The air intake orifice 59 is formed as two slots the height of each being approximately 7/32 inches (0.56 centimeters) and the width of each comprising an arc of approximately 120° degrees in the bottom most part of column segment 51. The air outlet 28 is a circular hole whose diameter can range from $\frac{1}{4}$ inches (0.64 centimeters) to $\frac{5}{8}$ inches (1.59 centimeters), however a diameter of approximately $\frac{3}{8}$ inches (0.95 centimeters) has been found to be the most effective. The air passage 19 is rectangular in cross section and possesses minimum dimensions of approximately $\frac{5}{8}$ inches $\times \frac{3}{4}$ inches (1.59 centimeters $\times$ 1.90 centimeters). Each column segment is approximately $1\frac{7}{8}$ inches (4.76 centimeters) in length with the lower calibrated uniform portion being a cylindrical section of approximately $1\frac{1}{8}$ inches (2.86 centimeters) in length and the upper free flow section being approximately $\frac{3}{4}$ inches (1.90 centimeters) in length. The inner diameter of each of the free flow sections is approximately 1.190 inches (3.02 centimeters), and the inner diameter of the lower calibrated cylindrical sections is varied for each column segment to provide the varying gap between the sphere and the column segment wall which calibrates the device. In calibrating the top most segment 21, the inner diameter of the lower calibrated cylindrical section 27 is formed to be 1.040 inches (2.64 centimeters) and results in an air flow rate of approximately 150 cubic centimeters per second. In calibrating the next below column segment 31, the inner diameter of the lower calibrated cylindrical section 37 is formed to be 1.080 inches (2.74 centimeters) and results in an air flow rate of approximately 500 cubic centimeters per second. In calibrating the next below column segment 41, the inner diameter of the lower calibrated cylindrical section 47 is formed to be 1.130 inches (2.87 centimeters) and results in an air flow rate of approximately 1000 cubic centimeters per second. It has been found to be unnecessary to provide a free flow section to column segment 51; its inner diameter is 1.190 inches (3.02 centimeters) and this results in an air flow rate of 1500 cubic centimeters per second.

The above flow rates are particularly selected for indicating the type of air flow, laminar, transitory or turbulent that the user is experiencing. Laminar flow is indicated at 150 cubic centimeters per second and is preferred for seriously ill users. The end of laminar flow and the beginning of the transition to turbulent flow is indicated by an air flow rate of approximately 500 cubic centimeters per second and is utilized by stronger users. The air flow rate of 1000 cubic centimeters per second approximates the end of the transitionary phase and the beginning of turbulent flow; this flow rate is utilized by still stronger users. The air flow rate of 1500 cubic centimeters per second indicates turbulent air flow to the user. In most cases it indicates that the user is breathing in a short, hard manner and, as longer, slower breathing is more beneficial for exercising the respiratory musculature and increasing the lung capacity, a return to the lower air flow rates is appropriate.

The device may be formed in sections by injection molding of any transparent high impact plastic. Ideally, front and rear portions of the structure may be individually formed by injection molding. Air flotation elements are then placed in the column segments of the air flow column; then the front and rear portions may be ultrasonically welded together. A tongue and groove 66 construction is formed in the joining walls 15, 16, 17, of the two injection molded portions to facilitate the ultrasonic welding of the portions.

It will be apparent from the foregoing description of the invention in its preferred form that it will fulfill all the objects attributable thereto, and while it is illustrated and described in detail, the invention is not to be limited to such details as have been set forth except as may be necessitated by the appended claims.

What I claim is:

1. An improved inhalation flow rate measuring device comprising
   a vertical air flow column defined by a series of column segments having cross-sectional dimensions which are uniform along at least a lower portion of the length of each of said column segments,
   means for inhaling air up through said column, and
   an air flotation element moveably disposed in each of said column segments, at least one stop member projecting from the sidewall adjacent the lower end of the lower portion of each column segment whereby each of said elements initially reside within the lower portion of said column segment and each of said elements being separately raiseable within its column segment,
   each of said elements being sized to fit within the uniform portion of the column segments with a relatively small gap disposed between said element and the interior wall of the uniform portion of said column segments whereby said element will rise within said column segment when the inhalation air flow rate through said gap is sufficient to raise said element,
   means associated with each of said column segments to permit the freeflow of air therethrough after said inhalation air flow rate through each of said segments has been exceeded, said free flowrate through each of said sections being greater than the maximum flow rate registerable by said device,
   each flotation element in each column segment having a different gap associated therewith whereby each of said elements is raisable by a different inhalation air flow rate through said column.

2. The improved inhalation flow rate measuring device of claim 1 wherein most of said column segments include an upper free flotation section and all of said segments have a lower uniform portion which is calibrated for the air flow rate which causes the air flotation element within the uniform portion to rise therein.

3. The improved inhalation flow rate measuring device of claim 1 wherein the air flotation elements are of an equal size and of uniform configuration and the cross-sectional dimensions of the uniform portions of the column segments vary from column segment to column segment.

4. The improved inhalation flow rate measuring device of claim 3 wherein said elements are lightweight spheres and said column is generally cylindrical in shape.

5. An improved inhalation flow rate measuring device including
   an air flow chamber in the form of a vertical column having a series of column segments each of which includes a cylindrical lower section and all but the bottom column segment include an upper free flotation section of larger cross-sectional area than said cylindrical lower section,
   a means for inhaling air up through said column, and
   a flotation sphere disposed in the cylindrical section of each of said segments, at least one stop member projecting from the sidewall of said cylindrical section adjacent the lower end of each lower section, said spheres being moveable from said cylindrical sections to said free flotation sections by the flow of air through said column, each of said spheres being sized to fit within said cylindrical section of said column segment with a relatively small gap disposed between said sphere and the interior wall of said cylindrical section thereby creating a cross-sectional air flow area surrounding said sphere whereby said sphere will rise within said column segment when the inhalation air flow rate through said cross-sectional air flow area is sufficient to raise said element, each of said sphere/segment combinations having a different cross-sectional area differential from each of the other sphere/segment combinations so that the sphere of each combination rises in its segment at a different rate of inhalation air flow through the column.

6. The improved inhalation flow rate measuring device of claim 5 wherein the segments of the column are arranged so that the flow indicators will register their respective air flow rates in progressive sequence.

7. The improved inhalation flow rate measuring device of claim 5 wherein the column is provided with a support base and an air communication channel to permit attachment of a hose and mouthpiece to the device proximate the base of the column for stability while activating the device at a distance therefrom.

8. The improved inhalation device of claim 7 wherein the structure of said device excepting said spheres is formed in two mating halves of injection molded clear plastic with said spheres being enclosed in said column segments between said halves prior to securing said halves together.

9. The improved inhalation flow rate measuring device of claim 7 wherein said hose is a flexible hollow inhalation tubing which may include a medicinal dispensing device and a dual valve disposed between said air communication channel and the mouthpiece attached to said tubing.

10. The improved inhalation flow rate measuring device of claim 5 wherein the said column contains a plurality of column segments each of which is calibrated to measure a specific air flow rate between 150 and 1500 cubic centimeters per second.

11. The improved inhalation device of claim 5 including an air filter to filter the air being inhaled through said device.

12. An improved inhalation flow rate measuring device comprising
- a molded clear plastic structure formed of mating halves and having a continuous vertical air flow column defined therein by a series of column segments each having a lower calibrated cylindrical section and all but the bottom column segment having upper free flotation sections of a larger cross-sectional area than its associated lower cylindrical section, each of said cylindrical sections having a different diameter,
- a multiple of equal sized lightweight air flotation spheres, one of said spheres being disposed in each of said cylindrical sections of each of said column segments, at least one stop member projecting from the sidewall of said cylindrical section adjacent the lower end of each cylindrical section, said spheres being arranged to rise in its cylindrical section when a predetermined air flow rate through said column is achieved, each of said spheres being sized to fit within the lower cylindrical section of the column segments with a relatively small gap disposed between said sphere and the interior wall of the lower cylindrical section of said column segment thereby creating a cross-sectional air flow area surrounding said sphere whereby said sphere will rise within said column segment when the inhalation air flow rate through said cross-sectional air flow area is sufficient to raise said sphere, each flotation sphere in each column segment having a different gap associated therewith whereby each of said spheres is raised by a different inhalation air flow rate through said column.
- said column segments being calibrated to measure air flow rates between 150 cc/sec and 1500 cc/sec with the lower flow rate column segments disposed at the top of said column and the higher flow rate column segments being sequentially disposed therebelow,
- an air outlet disposed at the top of said column and a mouthpiece connection orifice disposed near the bottom of said column to permit the attachment of a hose and mouthpiece thereto,
- a filter screen for filtering air drawn through said orifice, and
- an air communication passage interconnecting the air outlet and mouthpiece connection orifice whereby air inhaled through said hose and mouthpeice draws air up through said column.

13. The improved inhalation flow rate measuring device of claim 12 wherein said hose is a flexible hollow inhalation tubing which may include a medicinal dispensing device and a dual valve disposed between said air communication passage and the mouthpiece attached to said tubing.

* * * * *